United States Patent
Warburton

(10) Patent No.: US 6,358,384 B1
(45) Date of Patent: Mar. 19, 2002

(54) ELECTROCHEMICAL SENSOR FOR DETECTING A PREDETERMINED GAS

(75) Inventor: Piers Richard Grove Warburton, Coraopolis, PA (US)

(73) Assignee: National Draeger Incorporated, Pittsburgh, PA (US)

( * ) Notice: Subject to any disclaimer, the term of this patent is extended or adjusted under 35 U.S.C. 154(b) by 0 days.

(21) Appl. No.: 09/597,097

(22) Filed: Jun. 20, 2000

Related U.S. Application Data

(62) Division of application No. 08/891,235, filed on Jul. 10, 1997, now Pat. No. 6,098,523.

(51) Int. Cl.$^7$ .............................................. G01N 27/407
(52) U.S. Cl. ....................................................... 204/427
(58) Field of Search ........................... 204/427, 290.01; 73/1.04, 1.06, 1.07, 1.03, 1.05

(56) References Cited

U.S. PATENT DOCUMENTS

| | | | | |
|---|---|---|---|---|
| 4,227,484 A | * | 10/1980 | Dempsey et al. | |
| 4,267,030 A | * | 5/1981 | Breuer et al. | 204/278 |
| 4,695,361 A | * | 9/1987 | Grady | 204/415 |
| 4,828,671 A | * | 5/1989 | Lin et al. | 204/427 X |
| 4,839,015 A | * | 6/1989 | Wakematsu et al. | 204/290.1 |
| 4,874,500 A | * | 10/1989 | Madou et al. | 204/412 |
| 4,882,033 A | * | 11/1989 | Shibata et al. | 204/427 X |
| 5,061,631 A | * | 10/1991 | Calabrose | 73/1.06 X |
| 5,126,035 A | * | 6/1992 | Kiesele et al. | 204/415 |
| 5,314,605 A | * | 5/1994 | Matthiessen | 204/415 |
| 5,336,390 A | * | 8/1994 | Busack et al. | 204/431 |
| 5,505,837 A | * | 4/1996 | Friese et al. | 204/427 X |
| 5,573,648 A | * | 11/1996 | Shen et al. | 204/412 |
| 5,668,302 A | * | 9/1997 | Finbow et al. | 73/23.2 |
| 5,827,948 A | * | 10/1998 | Martell et al. | 73/31.06 |

FOREIGN PATENT DOCUMENTS

| | | | | |
|---|---|---|---|---|
| EP | 298570 A2 | * | 1/1989 | |
| GB | 2 235050 A | * | 2/1991 | |
| JP | 61-272649 | * | 12/1986 | 204/427 |
| JP | 62-218852 | * | 9/1987 | 204/431 |
| JP | 4-134234 | * | 5/1992 | |
| WO | 96/14576 | * | 5/1996 | |

* cited by examiner

Primary Examiner—Thomas P. Noland
(74) Attorney, Agent, or Firm—Cohen & Grigsby, P.C.

(57) ABSTRACT

A gas sensor (8) includes a body (10) that is shaped to define a chamber (14). An electrolyte (34) is contained in the chamber (14) and three electrodes (26, 28 and 30) that are located on an electrode substrate (24) are disposed in contact with the electrolyte. The body (10) is electrically connected to the three electrodes. A cover (36) engages the body (10) to enclose the chamber (14). A resistor array (58a–58n) is located between the cover (36) and the electrode substrate (24). The resistors (58a–58n) are coated with a compound that emits a predetermined gas in response to temperature increase. To test the sensor (8) voltage is selectively applied to the resistor array (58a–58n) to introduce the gas to the gas diffusion path of the sensor (8).

9 Claims, 2 Drawing Sheets

ELECTROCHEMICAL SENSOR FOR DETECTING A PREDETERMINED GAS

This application is a division application of U.S. application Ser. No. 08/891,235 filed Jul. 10, 1997 entitled "Testing Apparatus for Gas Sensors", now U.S. Pat. No. 6,098,523.

BACKGROUND OF THE INVENTION

1. Field of the Invention

The present invention relates to apparatus for testing gas sensors and, more particularly, apparatus for testing carbon monoxide gas sensors.

2. Description of the Prior Art

Health and safety hazards that are associated with exposure to carbon monoxide and other gases have led to the development of various types of gas detectors. Such devices are based on various technologies including infrared absorbance, electrochemical oxidation, metal oxide conductivity, and chemical color changes. The different technologies offer various advantages and disadvantages, but each generally requires periodic calibration. Even for those instruments in which calibration is not required, verification of the instrument's functionality is usually preferred. However, such calibration has not always been available.

Various calibration and verification tests have been used in the prior art. The exact mechanism of these tests depends on the sensor technology. Some testers were based on electrical property measurements such as electrical resistance or electrode capacitance as described in U.S. Pat. No. 5,202,637. Other tests are based on measurement of electrochemical properties. However, such prior art testers were subject to various difficulties and disadvantages. For example, such tests tended to provide a simple positive or negative result—if the result is negative the sensor is deemed to be non-functional. However, such prior art tests were designed to assess only selected failure modes. If the sensor were to fail in a non-design mode, the result would be a false-positive indication. For example, an electrochemical sensor would lose sensitivity and yield false-positive results to an electrical resistance or electrode capacitance test if the diffusion limiting membrane were blocked by foreign material. As another example, a number of sensors use catalysts that can be deactivated by poisoning agents. However, electrical tests of the sensor would not detect this fault.

Other sensor testers such as described in U.S. Pat. Nos. 4,151,739 and 4,267,030 relied on an electrochemical electrolysis cell that was incorporated into or near the sensor. The sensor was generally responsive to the gas that the electrolysis cell generated, but the test process was indirect because the generated gas was not the gas of interest. For example, one electrolysis cell described in European Patent Application EP0744620A1 produced hydrogen gas through the electrolysis of sulfuric acid. However, it was recognized that if the gas of interest was other than hydrogen, as, for example, carbon monoxide, it would be preferable to test the sensor by direct exposure to the gas of interest.

A more reliable test methodology is to expose the sensor to the target gas and monitor the sensor response. However, prior art methods generally required the use of heavy or bulky compressed gas cylinders or complex electrochemical reactions to generate the target gas. For example, carbon monoxide sensors in industrial applications are frequently exposed to carbon monoxide sourced from a gas cylinder. Moreover, convenient sources of the target gas are not always available. Thus, in some applications, as in residential usage, the carbon monoxide sensors frequently are never field calibrated at all.

Accordingly, there was a need in the prior art for a gas sensor tester that would expose sensors to the target gas and monitor the reaction of the sensor. Additionally, there was a need for a sensor tester that was relatively compact and light, that would work with various types of sensors, and that provided a reliable, repeatable test environment.

SUMMARY OF THE INVENTION

In accordance with the subject invention, apparatus for testing a gas sensor includes an array of electrical resistors that are attached to a base member. One end of each resistor is electrically connected to a common terminal and each resistor is coated with a compound that emits a predetermined gas in response to increases in temperature of the resistor.

Preferably, the testing apparatus further includes means for generating an electrical voltage. Also preferably, the coating compound includes a metal oxalate wherein the metal is selected from the group consisting of alkali metals and alkaline earth metals.

More preferably, the voltage generating means of the testing apparatus includes means for generating a voltage at a predetermined time in combination with an electrical network that is connected to the voltage generating means and to the array of electrical resistors, wherein the network selectively connects individual resistors of the array to the voltage generating means. Also, more preferably, the coating on the resistors is a compound that includes an oxalate salt of a metal, a binder, and a thickener.

Most preferably, the apparatus for testing the gas sensor is included in the gas diffusion path of a sensor of the type wherein electrolyte is maintained in the body of the sensor and a plurality of electrodes are in contact with the electrolyte. Also most preferably, the metal of the metal oxalate is selected from the group of sodium, lithium, calcium, potassium and magnesium.

Other objects and advantages of the invention disclosed herein will become apparent to those skilled in the art as a description of a preferred embodiment of the invention proceeds.

BRIEF DESCRIPTION OF THE DRAWINGS

The accompanying drawings illustrate a preferred embodiment of the invention wherein.

Description of a Preferred Embodiment

Figure 1:
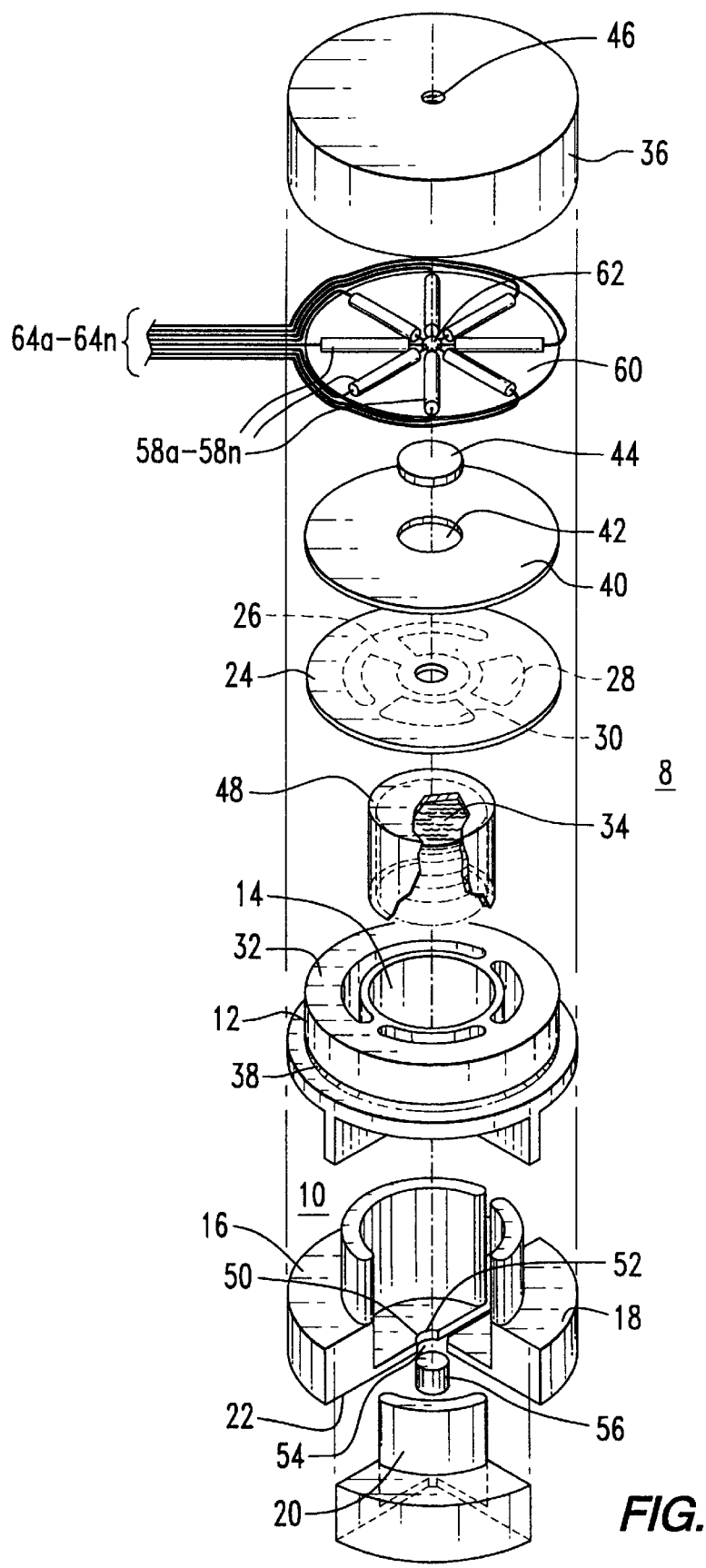
FIG. 1 is an exploded projection of a sensor that incorporates a resistor array in accordance with the preferred embodiment.
Figure 2:
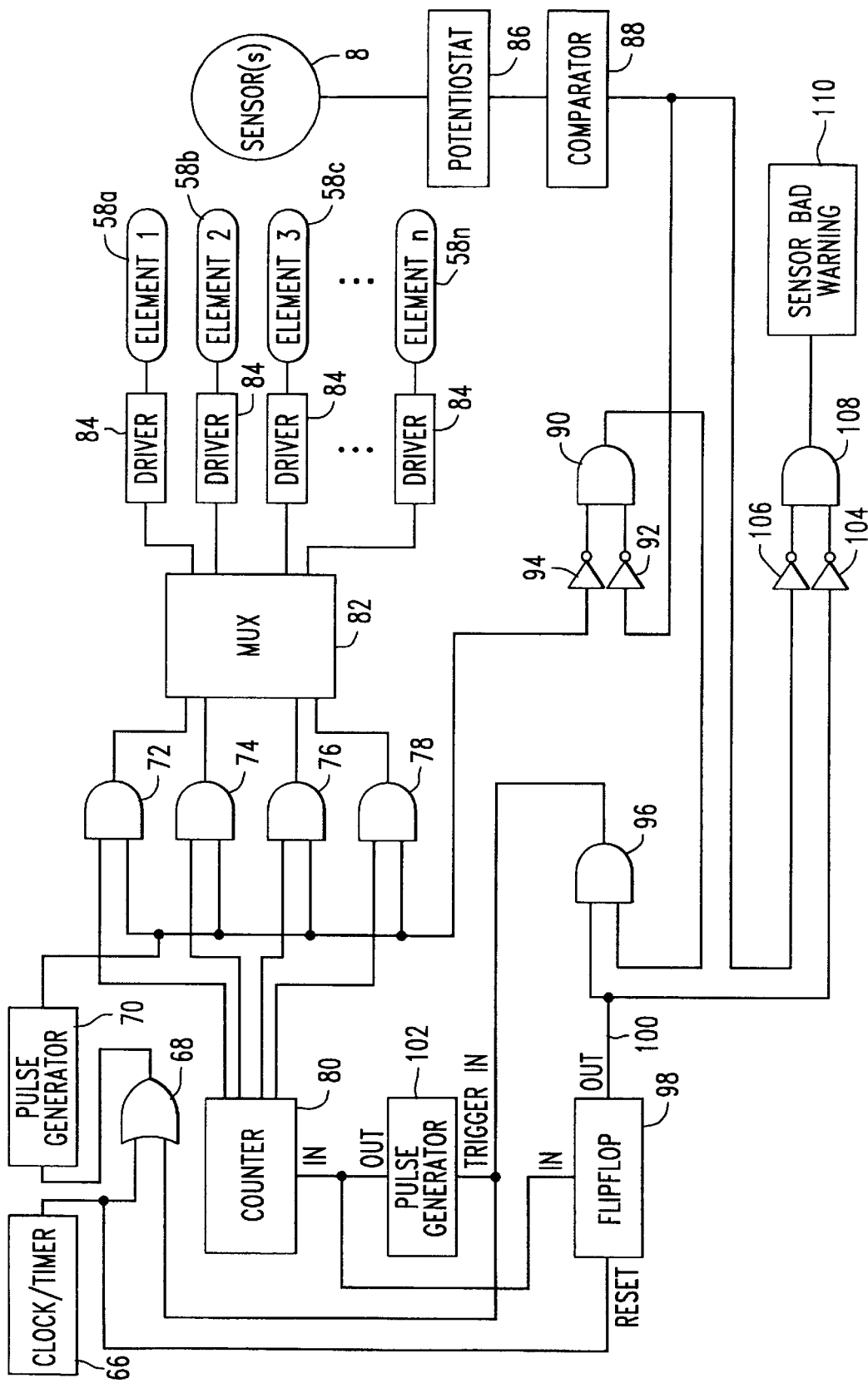
FIG. 2 is a schematic diagram illustrating the disclosed apparatus and method with selectively reusable elements for generating carbon monoxide.

A preferred embodiment of an automatic self-testing sensor in accordance with the invention is illustrated in FIGS. 1 and 2. Generally, the gas sensor is located in the proximity of the carbon monoxide generating elements herein disclosed so that the sensor is exposed to carbon monoxide generated from the elements. In the example of the preferred embodiment shown in FIGS. 1 and 2, the carbon monoxide generating element is incorporated integrally into the assembly of the sensor.

As shown particularly in FIG. 1, the sensor 8 has a body 10 that includes a first, generally cup-shaped, electrically non-conductive portion 12 that defines a well or chamber 14. As hereinafter more fully explained, non-conductive portion 12 cooperates with conductive portions 16, 18 and 20 to define an external surface 22. Body 10 has three electrically conductive portions 16, 18, and 20 that are spaced apart by non-conductive portion 12. Each of conductive portions 16, 18 and 20 serves as an electrical pathway from body 10. Conductive portions 16, 18 and 20 are electrically isolated from each other by the remaining non-conductive portion 12. The shape of conductive portions 16, 18 and 20 may be varied from those shown in FIG. 1.

The surface of an electrode substrate 24 that opposes body 10 has three conductive electrodes 26, 28 and 30 formed thereon. Electrode 26 is a working electrode, electrode 28 is a reference electrode and electrode 30 is a counter electrode. When electrode substrate 24 is located on the face 32 of non-conductive portion 12, electrodes 26, 28 and 30 are aligned and make contact with the portions 16, 18 and 20 of body 10.

An electrolyte 34 is maintained in chamber 14. A snap-fit cover 36 is retained on non-conductive portion 12 via a detent means such as an annular rib (not shown) that is integrally formed in cover 36. The annular rib matingly engages a complementary shaped means such as an annular groove 38 that is formed in non-conductive portion 12.

Gas-permeable substrate,24 and a rubber gasket 40 are disposed between non-conductive portion 12 and cover 36. Substrate 24 is in the shape of a flat circular disc. Rubber gasket 40 is also flat and circular with a central hole 42 formed therein to receive a cylindrical filter 44.

Cover 36 has an opening or sensing hole 46 formed therein. Opening 46 is located to Nose filter 44 to the ambient atmosphere that is to be sensed by the sensor. One purpose of filter 44, which may be a charcoal filter, is to filter out gases that are not to be sensed but that may interfere with sensing the gas(es) of interest. Filter 44 absorbs those gases before they diffuse into chamber 14 where the gas-sensing reaction takes place. Substrate 24 is hydrophobic to prevent the liquid electrolyte 34 from escaping from the sensor through opening 46. At the same time, substrate 24 allows external gases of interest to permeate there through and into chamber 14. Filter 44 does not filter the gas of interest and cooperates with hole 46 and gas-permeable substrate 24 to define a gas diffusion pathway between the exterior of the sensor and chamber 14.

The gas sensor further includes a wick 48. Wick 48 abuts the underside of substrate 24 and extends into electrolyte 34 in chamber 14. The purpose of wick 48 is to maintain the underside of substrate 24 (which has electrodes formed thereon) in fluid contact with electrolyte 34. Where the sensor is used to detect the presence of carbon monoxide, the electrolyte may be a 30% sulfuric acid aqueous solution.

Body 10 further includes a passageway such as bore 50 which communicates between an opening 52 in internal chamber 14 and an opening 54 in external surface, 22. Preferably, bore 50 is located in the center of non-conductive portion 12 and in opposing relationship to substrate 24 such that substrate 24 is oppositely disposed from internal chamber opening 52. However, other locations of bore 50 in non-conductive portion 12 are also within the scope of the subject invention.

A plug 56 is located in bore 50 so as to block the flow of electrolyte 34 from chamber 14 through bore 50 and out of the sensor. Plug 56 is made of a material that is both porous with respect to gases and hydrophobic with respect to electrolyte 34. Thus, plug 56 operates to block the flow of electrolyte 34 out of chamber 14 through bore 50, but permits the venting of gases out of chamber 14. In this way, gases that are expanding due to temperature changes in the sensor or gases generated by oxidation-reduction reactions within chamber 14 diffuse through plug 56 and pressure inside chamber 14 is in substantial equilibrium with ambient pressure. Plug 56 can be comprised of a porous material, such as Teflon, which is heat sealed to non-conductive portion 12 of body 10. Alternatively, plug 56 could be in the form of a membrane or a tube, also made of Teflon.

In operation of the sensor to detect a selected gas, such as carbon monoxide, a constant electrical voltage source is electrically connected to conductive contact portions 16 and 18 which are electrically connected to working electrode 26 and the reference electrode 28. If carbon monoxide passes through opening 46, it causes a chemical reaction at the interface of working electrode 26 and electrolyte 34. That reaction induces an electrical current between working electrode 26 and counter electrode 30. The induced current is detected and measured by a conventional current sensing circuit (not shown) that is attached to conductive portions 16 and 20 as is well known to those skilled in the art.

As particularly shown in FIGS. 1 and 2, a sensor 10 further includes a testing device to confirm that it is responsive to carbon monoxide. Specifically, carbon monoxide is generated from an array of elements 58a–58n that are attached to a base member such as a disk 60 that is located between cover 36 and gasket 40. In the preferred embodiment, disk 60 is a gas-permeable disk although a solid disk with a multiple of slots could also be used. Carbon monoxide generated from elements 58a–58n is emitted directly into the gas diffusion pathway defined by hole 46, filter 44 and porous substrate 24.

In accordance with the preferred embodiment, carbon monoxide generating elements 58a–58n are comprised of resistors that each have a surface coating. One end of each resistor is electrically connected to a common electrical terminal 62 and this opposite and of each resistor is connected to a separate electrical lead 64a–64n. The coating is a mixture of an oxalate salt of a metal selected from the group of alkali metals and alkaline earth metals, a binder and a thickener. Preferably, the metal oxalate is selected from the group of sodium oxalate, calcium oxalate, potassium oxalate and magnesium oxalate. Most preferably, sodium oxalate is used.

Also preferably, the binder is a negatively charged hydrophobic colloid comprising an aqueous suspension of polytetrafloroethelyene resin particles, non-ionic wetting agent and stabilizer. Teflon 30™ with 60% by weight of 0.05 to 0.5 um PTFE resin particles has been found to be a suitable binder. Most preferably, the thickener is a hydroxyethylcellulose such as Natrosol™ which is available from Aqualon.

An electrical power signal is applied to one of elements 58a–58n, so that the element is heated to about 150° C. to 300° C. The increase in temperature of the element results in the emission of carbon monoxide from the coating of the element directly into the gas diffusion path that is formed by hole 46, filter 44 and substrate 24.

It has been determined that the rate at which carbon monoxide is generated by elements 58a–58n decreases over the period that the element is heated. Therefore, to improve repeatability in the performance of the carbon monoxide sensor tester, the preferred embodiment discloses the use of an array of elements 58a–58n. As will be apparent to those skilled in the art, elements 58a–58n can be connected to a power source through a conventional switching circuit that would automatically switch to a new element 58a–58n each time the sensor is tested. Thus, a new element 58a–58n would be used with each test. However, elements 58a–58n can be used more than once for many applications. Therefore, in the preferred embodiment, the control circuitry described more particularly with regard to FIG. 2 provides for the reuse of each resistor in the array as long as the sensor tests positive. Once the sensor tests negative, the control circuitry allows for one re-test using a new resistor in the array. This re-test mechanism is intended to avoid false indications that the sensor is not working when such negative indication is actually caused by the insufficient generation of carbon monoxide by the generating element.

A preferred embodiment of control circuitry for the gas sensor tester is schematically illustrated in the FIG. 2. As will be apparent to those skilled in the art, FIG. 2 is a functional illustration of the circuitry wherein the logic gates, electronic components and circuitry can be variously embodied as, for example, in a microprocessor, or a microcontroller.

As illustrated in FIG. 2, a clock/timer 66 generates an electrical signal at a predetermined interval as, for example, once per month. This signal is conducted through OR gate 68 to pulse generator 70. Pulse generator 70 produces an output signal of predetermined voltage and duration in response to the signal from OR gate 68. The output signal is conducted to AND gates 72, 74, 76 and 78.

Counter 80 provides a binary gate incremental selection signal to AND gates 72, 74, 76, and 78. The selecting signal is the binary code designation for the gas generator element that is to be activated. The signal from counter 80 is provided coterminally with the signal from pulse generator 70 to AND gates 72, 74, 76 and 78. In this way, counter 80 and AND gates 72, 74, 76 and 78 gate the output of pulse generator 70 and provide a binary input signal from AND gates 72, 74, 76 and 78 to a multiplexer 82.

Multiplexer 82 is connected to a parallel array of drivers 84a–84n. Each of the drivers 84a–84n comprises a power circuit that is connected to a respective carbon monoxide generating element 58a–58n. Multiplexer 82 triggers one of drivers 84a–84n in response to the binary input signal from AND gates 72, 74, 76 and 78. Driver 84a–84n then energizes the respective carbon monoxide generating element 58a–58n to generate carbon monoxide.

Sensor 8 is controlled by a potentiostat 86. The output of potentiostat 86 Is compared to a reference potential in a comparator 88. If comparator 88 determines that the signal from potentiostat 86 indicates that sensor 8 is responsive to the carbon monoxide, a positive test is completed. However, if comparator 88 determines that the signal from potentiostat 86 indicates that sensor 8 is not responsive to the carbon monoxide, the test is initially negative and other failure modes are tested.

In the example of the preferred embodiment, if comparator 88 indicates that sensor 8 is non-responsive to the carbon monoxide, the output of comparator 88 is transmitted to AND gate 90 through an inverter 92. The output of pulse generator 70 is also connected to AND gate 90 through an inverter 94 so that AND gate 90 produces a signal when comparator 88 indicates a sensor failure and pulse generator 70 is low. The output of AND gate 90 is conducted to AND gate 96 which is also connected to the output of flip-flop 98. The initialization signal from clock/timer 66 to OR gate 68 and pulse generator 70 is also conducted to flip-flop 98 to reset the flip-flop and produce a high signal at output 100. The high signal from output 100 and the signal from AND gate 90 produce an output from AND gate 96.

The output from AND gate 96 is conducted to a second pulse generator 102 which provides an incremental signal to counter 80. At the same time, the output of pulse generator 102 changes the state of flip-flop 98 so that output 100 is low.

At the same time that the output from AND gate 96 triggers pulse generator 102 it is also conducted via or gate 68 to pulse generator 70 which initiates a retest of the firing circuit. However, since the state of flip-flop 98 has been changed, no subsequent retests can occur. That is because output 100 of flip-flop 98 is now low so that AND gate 96 will not produce further output. Instead, output 100 is conducted to inverter 104. A second inverter 106 is connected to the output of comparator 88 so that subsequent low signals from comparator 88 are inverted at inverter 106 and combined with the inverted signal from flip-flop 98 in AND gate 108 to trigger a bad sensor indicator 110.

While a presently preferred embodiment of the subject invention has been shown and described herein, it will be apparent to those skilled in the art, the subject invention can be otherwise variously embodied within the scope of the following claims.

I claim:

1. An electrochemical sensor for detecting a predetermined gas, said sensor comprising:

a sensor assembly that defines an internal chamber and a gas diffusion pathway between the external surface of the sensor and the internal chamber;

an electrolyte that is maintained in said chamber;

a plurality of electrodes that are disposed in contact with said electrolyte; and means for emitting the predetermined gas to the gas diffusion path, the emitting means being located in said sensor assembly and including at least one element that emits the predetermined gas in response to an electrical power signal, said element being a resistor that is coated with a compound that includes the oxalate salt of a metal selected from the group consisting of alkali metals and alkaline earth metals.

2. The sensor of claim 1 wherein said metal oxalate is selected from the group consisting of sodium oxalate, lithium oxalate, calcium oxalate, potassium oxalate and magnesium oxalate.

3. An electrochemical sensor for detecting a predetermined gas, said sensor comprising:

a sensor assembly that defines an internal chamber and a gas diffusion pathway between the external surface of the sensor and the internal chamber, said sensor assembly further including a plurality of electrically conductive portions and an electrically non-conductive portion that is spaced between said electrically conductive portions, said sensor assembly also including a cover that mechanically urges said electrodes against said electrically conductive portions;

an electrolyte that is maintained in said chamber;

a plurality of electrodes that are disposed in contact with said electrolyte, said electrodes being mounted in a substrate; and means for emitting the predetermined gas to the gas diffusion path, the emitting means being located between the cover of said sensor assembly and the substrate wherein said electrodes are mounted, said emitting means including at least one element that emits the predetermined gas in response to an electrical power signal.

4. The sensor of claim 3 wherein said electrically conductive portions and said electrically non-conductive portion of said sensor assembly cooperate to define the internal chamber of said sensor assembly.

5. The sensor of claim 4 wherein each of said plurality of electrodes is electrically connected to a respective one of said electrically conductive portions of said sensor assembly.

6. The gas sensor of claim 3 wherein said cover engages a rubber gasket that is disposed between said substrate and said cover.

7. The sensor of claim 6 wherein the means for emitting a predetermined gas comprises an array of resistors that are located between the cover and the substrate, said resistors having a coating of a compound that emits a predetermined gas in response to increases in temperature.

8. The sensor of claim 7 wherein said compound includes the oxalate salt of a metal selected form the group consisting of alkali metals and alkaline earth metals.

9. The sensor of claim 8 wherein said metal oxalate is selected from the group consisting of sodium oxalate, lithium oxalate, calcium oxalate, potassium oxalate and magnesium oxalate.

* * * * *